United States Patent
Stickels et al.

(10) Patent No.: US 6,566,575 B1
(45) Date of Patent: May 20, 2003

(54) PATTERNED ABSORBENT ARTICLE FOR WOUND DRESSING

(75) Inventors: Steven C. Stickels, Woodbury; Peter M. Seiler, Minneapolis; Stephen E. Krampe, Maplewood; Scott A. Burton, Woodbury, all of MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/505,046

(22) Filed: Feb. 15, 2000

(51) Int. Cl.[7] .......................... A61F 13/00; A61F 13/15
(52) U.S. Cl. .......................... 602/41; 602/42; 604/304; 604/358
(58) Field of Search .................. 602/41–59; 604/304, 604/307, 368, 387; 424/443, 445, 446, 447, 448

(56) References Cited

U.S. PATENT DOCUMENTS

| | | |
|---|---|---|
| 1,956,695 A | 5/1934 | Reinitz |
| 1,967,923 A | 7/1934 | Connolly |
| 2,893,388 A | 7/1959 | Ganz |
| 2,896,618 A | 7/1959 | Schaefer |
| 2,923,298 A | 2/1960 | Dockstader et al. |
| RE24,906 E | 12/1960 | Ulrich .......................... 206/59 |
| 3,018,881 A | 1/1962 | Wall ............................ 206/56 |
| 3,073,304 A | 1/1963 | Schaar |
| 3,121,021 A | 2/1964 | Copeland .................... 119/112 |
| 3,285,245 A | 11/1966 | Eldredge et al. |
| 3,389,827 A | 6/1968 | Abere et al. .................. 220/53 |

(List continued on next page.)

FOREIGN PATENT DOCUMENTS

| | | |
|---|---|---|
| CA | 1339479 | 9/1997 |
| EP | 051935 | 11/1986 |
| EP | 269071 | 6/1988 |
| EP | 0768071 | 4/1997 |
| WO | WO 87/01029 | 2/1987 |
| WO | WO 90/10424 | 9/1990 |
| WO | WO 93/04649 | 3/1993 |
| WO | WO 94/17765 | 8/1994 |
| WO | WO 96/29035 | 9/1996 |
| WO | WO 97/11658 | 4/1997 |
| WO | WO 97/42917 | 11/1997 |
| WO | WO 97/42985 | 11/1997 |
| WO | WO 98/09666 | 3/1998 |
| WO | WO 98/17328 | 4/1998 |
| WO | WO 98/28013 | 7/1998 |
| WO | WO 99/06077 | 2/1999 |
| WO | WO 99/08724 | 2/1999 |
| WO | WO 99/13865 | 3/1999 |
| WO | WO 99/13866 | 3/1999 |
| WO | WO 99/36017 | 7/1999 |

OTHER PUBLICATIONS

S. Thomas, "Wound Management and Dressings", *The Pharmaceutical Press*, 1990, pp. 25–61, 81–87.

"Hydorgels", *Kirk–Othmer Encyclopedia of Chemical Technology*, 4th Edition, vol. 7, John Wiley and Sons, New York, pp. 783–807.

"Contact Lenses", *Kirk–Othmer Encyclopedia of Chemical Technology*, 4th Edition, vol. 7, John Wiley and Sons, New York, pp. 204–207.

C. Hansson, "Interactive Wound Dressings–A Practical Guide to Their Use in Older Patients", *Drugs & Aging* 1997 Oct.; 11(4), pp. 271–284.

D.A. Ladin, "Understanding Dressings", *Clinics in Plastic Surgery*, vol. 25, No. 3, Jul. 1998, pp. 433–441.

G. Sussman, "Management of the Wound Environment", pp. 201–209.

*Primary Examiner*—Kim M. Lewis
(74) *Attorney, Agent, or Firm*—Kent S. Kokko

(57) ABSTRACT

An absorbent dressing comprising a hydrophilic gel absorbent layer having a patterned surface on at least one major surface thereof is provided. The patterned surface allows greater surface area for absorption of wound exudate when oriented toward the wound surface, while reducing the absorbent surface area in direct or indirect contact with the wound.

23 Claims, 1 Drawing Sheet

U.S. PATENT DOCUMENTS

| | | |
|---|---|---|
| 3,521,631 A | 7/1970 | Gardner et al. |
| 3,645,835 A | 2/1972 | Hodgson ............... 161/146 |
| 3,689,346 A | 9/1972 | Rowland ............... 156/245 |
| 3,870,041 A | 3/1975 | Davies |
| 3,888,247 A | 6/1975 | Stenvall |
| 3,972,328 A | 8/1976 | Chen |
| 4,076,663 A | 2/1978 | Masuda et al. ......... 260/17.4 |
| 4,112,213 A | 9/1978 | Waldman ............... 526/279 |
| 4,181,127 A | 1/1980 | Linsky et al. |
| 4,300,820 A * | 11/1981 | Shah ...................... 351/160 |
| 4,499,896 A | 2/1985 | Heinecke |
| 4,538,603 A | 9/1985 | Pawelchak et al. |
| 4,598,004 A | 7/1986 | Heinecke ............... 428/40 |
| 4,738,257 A | 4/1988 | Meyer et al. |
| 4,773,903 A | 9/1988 | Weisman et al. ....... 604/368 |
| 4,798,604 A | 1/1989 | Carter ................... 604/383 |
| 4,849,458 A | 7/1989 | Reed et al. ............ 521/159 |
| 4,909,243 A | 3/1990 | Frank et al. |
| 4,909,244 A | 3/1990 | Quarfoot et al. |
| 4,952,618 A | 8/1990 | Olsen ..................... 524/17 |
| 4,956,350 A | 9/1990 | Mosbey .................. 514/55 |
| 4,979,946 A | 12/1990 | Gilman .................. 604/307 |
| 4,986,496 A | 1/1991 | Marentic et al. ....... 244/130 |
| 4,995,382 A | 2/1991 | Lang et al. |
| 5,018,515 A | 5/1991 | Gilman |
| 5,059,424 A | 10/1991 | Cartmell et al. ....... 424/443 |
| 5,125,401 A | 6/1992 | Gerhartl |
| 5,175,030 A | 12/1992 | Lu et al. ................. 428/30 |
| 5,183,597 A | 2/1993 | Lu .......................... 264/1.4 |
| 5,254,723 A | 10/1993 | Yang et al. ............. 560/240 |
| 5,328,450 A | 7/1994 | Smith et al. ............ 602/59 |
| 5,409,472 A * | 4/1995 | Rawlings et al. ....... 604/307 |
| 5,486,158 A | 1/1996 | Samuelsen |
| 5,501,661 A | 3/1996 | Cartmell et al. |
| 5,531,855 A | 7/1996 | Heinecke et al. ....... 156/252 |
| 5,603,946 A | 2/1997 | Constantine ............. 424/445 |
| 5,614,310 A | 3/1997 | Delgado et al. ......... 428/316.6 |
| 5,618,281 A * | 4/1997 | Betrabet et al. ......... 604/387 |
| 5,622,711 A | 4/1997 | Chen ...................... 424/445 |
| 5,653,699 A | 8/1997 | Reed et al. ............. 604/307 |
| 5,681,579 A * | 10/1997 | Freeman ................. 424/448 |
| 5,691,846 A | 11/1997 | Benson, Jr. et al. ...... 359/530 |
| 5,695,777 A | 12/1997 | Donovan et al. ......... 424/443 |
| 5,733,570 A | 3/1998 | Chen et al. .............. 424/445 |
| 5,738,642 A | 4/1998 | Heinecke et al. ......... 602/58 |
| 5,782,787 A | 7/1998 | Webster .................. 602/46 |
| 5,795,345 A * | 8/1998 | Mizutani et al. ......... 604/389 |
| 5,811,116 A | 9/1998 | Gilman et al. ........... 424/443 |
| 5,849,325 A | 12/1998 | Heinecke et al. ........ 424/443 |
| 5,897,516 A * | 4/1999 | Kadash et al. ........... 602/41 |
| 5,932,200 A | 8/1999 | Reich et al. ............. 424/65 |
| 5,941,840 A | 8/1999 | Court et al. ............. 602/47 |
| 5,981,822 A * | 11/1999 | Addison .................. 602/41 |

\* cited by examiner

PATTERNED ABSORBENT ARTICLE FOR WOUND DRESSING

The present invention is directed to an absorbent article used as a wound dressing. More particularly this invention is directed to an absorbent article having an absorbent, hydrophilic gel layer having a patterned surface.

Historically, exudate from a wound has been dealt with by absorbing it using a dressing containing some type of absorbent material. Examples include dressings such as those shown in U.S. Pat. No. 2,893,388, U.S. Pat. No. 3,018,881 and U.S. Pat. No. 3,073,304. All of these dressings contain a padded absorbent material attached to an adhesive tape backing. The padded absorbent material is applied to the wound to absorb the wound exudate. A difficulty with this type of dressing is that as the wound heals, the scab typically forms in and as part of the pad. Thus, when the dressing is removed, the scab is removed. The disclosures of U.S. Pat. No. 2,923,298, U.S. Pat. No. 3,285,245 and U.S. Pat. No. 3,870,041 have addressed this problem by providing a porous film between the absorbent material and the wound to reduce the likelihood that a scab formed will become attached to the absorbent material.

U.S. Pat. No. 3,888,247 discloses placing a microporous material over the wound and then applying a perforated urethane film containing a wound dressing made in accordance with U.S. Pat. No. 3,285,245 over the microporous tape applied to the wound. U.S. Pat. No. 1,967,923 contains a cellulose sheet membrane or film which protects the dressing and allows air to circulate over the wound. Other wound dressings comprising films are disclosed in U.S. Pat. Nos. 3,645,835, 4,499,896, 4,598,004, and 5,849,325.

A difficulty with dressings which comprise a thin film applied to the wound involves a pooling of exudate under the film if the wound is producing a large amount of exudate. This can result in loosening or removal of the wound dressing. An attempted solution to this problem is provided in U.S. Pat. No. 1,956,695 which discloses a round plaster which contains a rubber film which expands to allow pus to collect under it. This plaster allows the exudate to remain against the wound. Another attempted solution is provided in U.S. Pat. No. 3,521,631 which discloses an impervious sheet placed over a wound with an absorbent material extending over the impervious sheet and around its edges to allow wound exudate to pass into the absorbent material at the edges of the impervious sheet. This entire structure is covered with a backing sheet which is impervious and occlusive. An alleged improvement of the device disclosed in U.S. Pat. No. 3,521,631 is that disclosed in U.S. Pat. No. 4,181,127. An imperforate film of polyurethane contacts the wound which has an absorbent material over it that overlaps the film edges so that the exudate is passed to the absorbent material at the edges of the film. Adhesive tape can be applied over the top of the combination as long as the moisture vapor transmission of the total construction is at least 0.06 mg/cm$^2$ /hour.

More recently the use of so-called "occlusive" dressings for pressure sores and ulcers have gained increasing acceptance. A number of wound dressings of this kind are available commercially. Most of these products are formed from several layers, including at least an inner skin-contacting layer and an outer backing layer. The dressing is applied as a cover for the sore or ulcer in a size providing a margin around the wound area that adhesively seals to the skin. The inner layer contains water-absorptive materials, so that fluid from the wound is absorbed into the layer, making it possible to keep the dressing in place for at least several days. Such occlusive dressings tend to promote healing by maintaining the wound under moist conditions, and serve as a barrier against bacterial infection.

While previously known occlusive dressings have overcome some of the problems associated with the management of wounds, they have been found to have certain limitations or disadvantages that have not heretofore been overcome. Absorption of fluid by the portion of the absorptive layer in contact with the wound causes the central portion of the applied dressing to swell and push against the wound. Continued swelling can induce separation of the adhesive layer from the skin outside of the wound area. Fluid may enter between the inner surface absorptive layer and the surrounding skin, working its way outward until it reaches the periphery of the dressing. A primary concern is that such leakage provides a tract for the invasion of pathogenic microorganisms. Also, such leakage can cause skin maceration, leading to enlargement of the wounds.

Leakage of the wound exudate is objectionable because of its unpleasant odor soils bedding and clothing leading to increased costs because of dressing changes. Further, the dressing must be replaced when leakage develops. The more absorptive material included in the absorptive layer, the greater its fluid-absorbing capacity, but too much absorbency can limit the life of the dressing because of the swelling-induced leakage.

In the management of pressure sores, it is desirable that the occlusive dressing be removable in one piece. This minimizes the need to cleanse the wound between dressing applications. At the same time, stripping of the central portion of the dressing from the wound can damage healing tissue.

In an effort to ameliorate some of the foregoing difficulties, a wound care product in current use utilizes a hydrocolloid absorbent that partially loses its integrity after absorbing wound fluid. The portion of the absorbent in contact with the wound is converted to a gel-like material. When the dressing is removed, a portion of this gel material is left in the wound, and must be removed to permit examination and/or before applying another dressing. A wound dressing of the decomposing gel-forming type is disclosed in U.S. Pat. No. 4,538,603. This dressing utilizes a three-layer composite, also generally described in U.S. Pat. No. 3,972,328. A layer of semi-open cell foam material is interposed between the hydrocolloid-containing adhesive layer and an outer film layer. The hydrocolloid material may disintegrate within the adhesive layer, into a non-structural gel on absorbing wound fluid.

An alternative approach is to use a porous, non-adherent skin-contacting layer in an attempt to separate the hydrophilic absorbent material from the wound. However, as the absorbent layer expands on contact with wound exudate, the absorbent tends to swell and protrude or "mushroom", i.e. expand and extend through the pores of the barrier film and contact the wound surface. As with the previous hydrocolloid dressings, effective cleansing is required to wash out the absorbent material from the wound, which must be carried out carefully and gently to avoid damage to the wound bed and newly formed tissue.

SUMMARY OF THE INVENTION

This invention provides an absorbent dressing comprising a hydrophilic gel absorbent layer having a patterned surface on at least one major surface thereof. The patterned surface allows greater surface area for absorption of wound exudate when oriented toward the wound surface, while reducing the absorbent surface area in direct or indirect contact with the wound. More significantly, the patterned surface reduces the propensity of the absorbent layer to swell and push against the wound, avoids mushrooming (i.e. expansion of the gel layer through a porous film) and further avoids premature separation of the adhesive layer from the skin. By providing the gel absorbent layer with a patterned surface, the gel may swell into the voids of the patterned surface. Further, the patterned absorbent layer tends to maintain its integrity when hydrated and has a reduced propensity to disintegrate into smaller particles.

The present invention also provides a wound dressing comprising a fluid permeable facing layer and moisture vapor permeable backing layer with the absorbent layer disposed between the two. Preferably the backing layer is both moisture vapor permeable and liquid impermeable. The wound dressing may further comprise a layer of pressure sensitive adhesive to secure the dressing to the skin.

The wound dressing of the present invention advantageously can remove excess exudate from the wound, maintain a moist wound environment, allows gas exchange so that oxygen, water vapor and carbon dioxide can pass through the dressing, is thermally insulating to maintain the wound at body temperature, may be impermeable to liquids and microorganisms to minimize contamination and infection, may be non-adherent to the wound so that no damage is done to the granulating tissue, and minimizes the need to cleanse the wound of dressing material. Further the wound dressing of the present invention can be essentially transparent to allow visual inspection of the wound without removal of the wound dressing.

DETAILED DESCRIPTION

Figure 1:
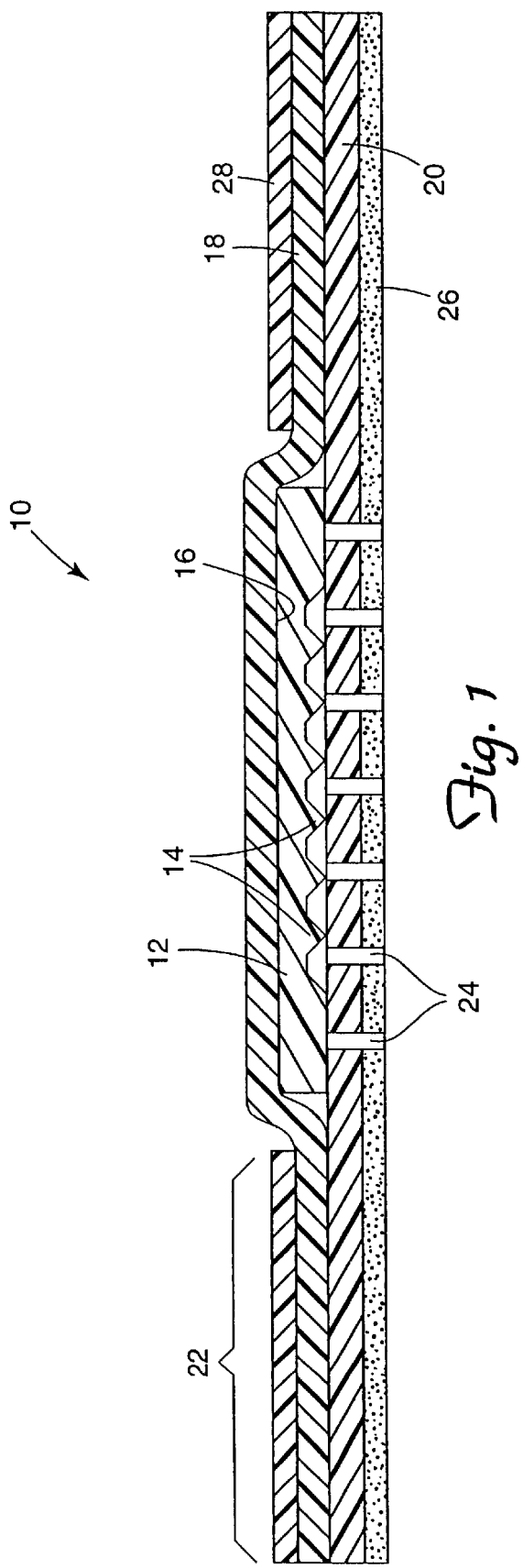
FIG. 1 is a cross-section of a wound dressing of the invention

As used herein "hydrophilic gel" refers to hydrophilic polymeric material that is capable of swelling on contact with water, but does not dissolve in water. The term is used regardless of the state of hydration. Useful hydrophilic gel materials are substantially continuous, i.e. lacking a cellular or voided internal structure and thus are generally in the form of a solid or semi-solid. However, minor defects such as entrapped air bubbles or fractures in the gel are acceptable. As used herein, the term "hydrophilic gel" is meant to include hydrocolloids, hydrogels and combinations thereof without limitation so long as the material is physiologically tolerable and clinically acceptable. Hydrocolloid gels, or simply hydrocolloids, are defined herein as hydrophilic gels that include a colloid, i.e., a suspension of finely divided particles in a continuous medium. Hydrogels are defined herein as hydrophilic gels that comprise at least one hydrophilic polymer. Useful hydrophilic gel material will absorb at least 100% by weight, preferably at least 300% by weight, at saturation according to the method described in U.S. Pat. No. 5,733,570, column 6.

As used herein the terms "front surface" and "back surface" used with respect to the hydrophilic gel layer, the facing layer and the backing layer, refers to the major surface of the indicated layer that, in use, faces toward the wound surface or away from the wound surface, respectively.

Suitable hydrocolloids include, but are not limited to, natural gums, such as plant exudates (gum arabic, ghatti, karaya, and tragacanth); plant seed gums (guar, locust bean and acacia), seaweed extracts (agar, algin, alginate salts and carrageenin), cereal gums (starches and modified starches), fermentation or microbial gums (dextran and xanthan gum), modified celluloses (hydroxymethylcellulose, microcrystalline cellulose and carboxymethylcellulose) pectin, gelatin, casein and synthetic gums (polyvinylpyrrolidone, low methoxyl pectin, propyleneglycol alginates, carboxymethyl locust bean gum and carboxymethyl guar gum) and like water-swellable or hydratable hydrocolloids. The term hydrocolloid is. used regardless of the state of hydration.

Hydrocolloids are typically dispersed in a continuous phase or matrix of a hydrophobic polymeric material, such as natural or synthetic rubbers, block copolymers of styrene/butadiene or ethylene/vinyl acetate copolymers. Such compositions comprising a hydrocolloid and hydrophobic polymers are especially useful in retaining structural integrity of the absorbent layer. In particular such compositions provide high wet integrity, and thus provide dressings that maintain their form and impart a minimum amount of hydrocolloid residue, if any, to a wound and the surrounding skin. In addition, the compositions can be formulated to provide a wide range of absorbency and still maintain optimal wet integrity.

Useful hydrophobic polymers are unsaturated aliphatic polymers. The hydrophobic unsaturated aliphatic polymer can comprise either a straight-chain or a branched chain unsaturated aliphatic homo- or copolymer, or a combination thereof. In addition, the hydrophobic unsaturated aliphatic polymer can be substituted along its polymer chain with another moiety, such as chlorine, fluorine, or a lower alkyl, and still be considered to fall within the scope of the present invention. Substitution of other monomers within the polymer chain of the polymer (e.g., random, block, and sequential copolymers) is considered to be within the present invention.

As used herein, a hydrophobic unsaturated aliphatic polymer refers to olefin polymers, that are substantially water insoluble, and which exhibit a significant degree of unsaturated double bonds in the polymer chain and/or branched side chains. Potentially any degree of unsaturation may be considered as part of the present invention.

The hydrophobic unsaturated aliphatic polymer may comprise an elastomeric polymer. Nonlimiting examples of suitable elastomeric homopolymers include polymers and copolymers of polyisoprene, polybutadiene, and combinations thereof, with polyisoprene being preferred. Polyisoprene is commercially available from a number of sources, including Goodyear Chemical Co., Akron, Ohio, under the NATSYN trademark, including Natsyn resin Nos. 2200, 2205, and 2210.

The hydrophilic gel may comprise from about 20 percent to about 50 percent by weight of the hydrophobic polymer and about 80 to 50 percent by weight of the hydrocolloid. For wound dressing applications, it is desirable to limit the amount of hydrophobic polymer present, in order to maximize the level of hydrocolloid, thereby achieving maximum fluid absorbency.

The hydrophobic polymer and hydrocolloid may be combined, for example by milling, and this mixture of ingredients is exposed to a dose of ionizing radiation which chemically cross-links the hydrophobic polymer component, thereby yielding a high integrity hydrocolloid composition. While it is preferable to irradiate the ingredients after mixing and imparting the desired pattern onto the surface, it is possible to irradiate the ingredients to partially crosslink prior to mixing and/or imparting of the patterned surface. However, in such an instance, the complete curing of the ingredients may be done in stages, and the resulting mixture may still need to be exposed to a further dose of radiation to deliver the desired structural integrity.

Hydrogels are hydrophilic polymers characterized by their hydrophilicity (i.e capable of absorbing large amounts of fluid such as wound exudate) and insolubility in water: swelling in water but generally preserving their shape. The hydrophilicity is generally due to groups such as hydroxyl, carboxy, carboxamido, and esters, among others. On contact with water, the hydrogel assumes a swollen hydrated state that results from a balance between the dispersing forces acting on hydrated chains and cohesive forces that do not prevent the penetration of water into the polymer network. The cohesive forces are most often the result of crosslinking, but may result from electrostatic, hydrophobic or dipole-dipole interactions.

Useful classes of hydrogels includes those polymers and copolymers derived from acrylic and methacrylic acid ester, including hydroxyalkyl (meth)acrylates, 2-(N,N-dimethylamino)ethyl methacylate, ω-methacryloyloxyalkyl sulfonates (generally crosslinked with diacrylate or divinylbenzene), polymers and copolymers of substituted and unsubstituted acrylamides, polymers and copolymers of N-vinylpyrrolidinone, and polyelectrolyte complexes. Hydrogels are described in greater detail in *Hydrogels*, Kirk-Othmer Encyclopedia of Chemical Technology, $4^{th}$ Edition, vol. 7, pp. 783–807, John Wiley and Sons, New York. The term hydrogel is used herein regardless of the state of hydration.

The hydrogel will generally comprise a substantially water-insoluble, slightly crosslinked, partially neutralized, gel-forming polymer material. Such polymer materials can be prepared from polymerizable, unsaturated, acid- and ester-containing monomers. Thus, such monomers include the olefinically unsaturated acids, esters and anhydrides which contain at least one carbon to carbon olefinic double bond. More specifically, these monomers can be selected from olefinically unsaturated carboxylic acids, carboxylic esters, carboxylic acid anhydrides; olefinically unsaturated sulfonic acids; and mixtures thereof.

Olefinically unsaturated carboxylic acid, carboxylic acid ester and carboxylic acid anhydride monomers include the acrylic acids typified by acrylic acid itself, methacrylic acid, ethacrylic acid, alpha-chloroacrylic acid, alpha-cyano acrylic acid, beta-methyl-acrylic acid (crotonic acid), alpha-phenyl acrylic acid, beta-acryloxy propionic acid, sorbic acid, alpha-chloro sorbic acid, angelic acid, cinnamic acid, p-chloro cinnamic acid, beta-styryl acrylic acid (1-carboxy-4-phenyl-1,3-butadiene), itaconic acid, citraconic acid, mesaconic acid, glutaconic acid, aconitic acid, maleic acid, fumaric acid, tricarboxy ethylene and maleic acid anhydride.

Olefinically unsaturated sulfonic acid monomers include aliphatic or aromatic vinyl sulfonic acids such as vinylsulfonic acid, allyl sulfonic acid, vinyltoluenesulfonic acid and styrene sulfonic acid; acrylic and methacrylic sulfonic acid such as sulfoethyl acrylate, sulfoethyl methacrylate, sulfopropyl acrylate, sulfopropyl methacrylate, 2-hydroxy-3-acryloxy propyl sulfonic acid, 2-hydroxy-3-methacryloxy propyl sulfonic acid and 2-acrylamido-2-methyl propane sulfonic acid.

Of all the foregoing unsaturated, acid-containing monomers, preferred monomers include acrylic acid, methacrylic acid, N-vinyl pyrrolidinone, lower alkyl acrylamides, and 2-acrylamido-2-methyl propane sulfonic acid. Acrylic acid itself is especially preferred for preparation of the hydrophilic gel. Particularly useful compositions are those described in U.S. Pat. No. 5,733,570 (Chen) containing a blend of hydrophilic polymers and hydrophobic polymers.

In the hydrogels used herein, the polymeric component formed from unsaturated, acid-containing monomers may be grafted on to other types of polymer moieties such as starch or cellulose. Hydrogels which can be prepared from the foregoing types of monomers include hydrolyzed acrylonitrile grafted starch, acrylic acid grafted starch, polyacrylates, isobutylene maleic anhydride copolymers and combinations thereof.

Whatever the nature of the basic polymer components of the hydrogel used herein, such materials will preferably be slightly cross-linked. Cross-linking serves to render the hydrogels used in this invention substantially water-insoluble, and cross-linking thus in part determines the gel volume and extractable polymer characteristics of the hydrogels formed. Suitable cross-linking agents are well known in the art and include, for example, (1) compounds having at least two polymerizable double bonds; (2) compounds having at least one polymerizable double bond and at least one functional group reactive with the acid-containing monomer material; (3) compounds having at least two functional groups reactive with the acid-containing monomer material; and (4) polyvalent metal compounds which can form ionic cross-linkages. Cross-linking agents of the foregoing types are described in greater detail in U.S. Pat. No. 4,076,663 (Masuda et al), incorporated herein by reference. Useful cross-linking agents are the diol polyesters of unsaturated mono- or polycarboxylic acids with polyols, the bisacrylamides and the di- or triallyl amines. Especially preferred cross-linking agents are N,N'-methylenebisacrylamide, trimethylol propane triacrylate polyethylene oxide diacrylates, triallyl amine, and other di- and tri-functional monomers.

The cross-linking agent will generally comprise from about 0.001 mole percent to 5 mole percent of the resulting hydrogel. More preferably, the cross-linking agent will comprise from about 0.01 mole percent to 3 mole percent of the hydrogel used herein.

The slightly cross-linked, hydrogel-forming polymer gelling agents used in the present invention may be employed in their partially neutralized form. Suitable salt-forming cations include, but are not limited to, alkali metal, ammonium, substituted ammonium and amines. This percentage of the total monomers utilized that are neutralized acid group-containing monomers is referred to herein as the "degree of neutralization."

As a subset of hydrogels, alginates are a special variation supplied as a fibrous material manufactured from varieties of plants, especially extracts of kelp or seaweed. Sodium alginate produce viscous liquids and calcium alginate forms gels. Consequently sodium and calcium alginate salts can be blended to achieve the desired level of gelation. Alginates are typically available in substantially dehydrated form and swell upon absorption of wound exudate.

Other suitable hydrogels are polyacrylic acid allylsucrose copolymers and salts thereof. These so-called carbomers, for example, are the homopolymers of acrylic acid crosslinked with an allylether of pentaerythritol, an allylether of sucrose or an allylether of propylene and are sold in varying viscosities and molecular weights under the trademark CARBOPOL by B.F. Goodrich Company (Cleveland, Ohio). Also useful are non-drying, aqueous jellies of glycerol polyacrylate sold under the trademark HISPAGEL in varying viscosities by Hispano Quimica S.A. (Barcelona, Spain), and gels of radiation crosslinked hydrophilic polyoxyethylene described in U.S. Pat. No. 3,419,006 to King and sold under the Trademark VIGILON by C.R. Bard, Inc. (Murray Hill, N.J.).

The pattern imparted to the surface of the hydrophilic gel absorbent layer may be any suitable preselected three-dimensional pattern that increases the surface area available for absorption and which reduces swelling into the wound, retards mushrooming, and/or enhances gel layer integrity upon hydration. The pattern comprises an array of pattern elements that include, but are not limited to, ridges, channels, mounds, peaks, hemispheres, pyramids, cylinders, cones, blocks, and truncated variations and combinations thereof. The pattern may further comprise apertures having a predetermined shape and size extending through the thickness of the absorbent gel layer.

The specific pattern element is advantageously chosen to present minimal surface area in contact with the wound or the facing film if present. The minimal surface area further retards the tendency of the hydrophilic gel to swell into the wound, mushroom, or adhere to the wound site. Especially useful elements include pyramids, cones and truncated versions thereof, and ridges which are triangular in cross section. The elements may be random or non-random in the x direction, the y direction, or both. For ease of manufacture, it is preferable that the pattern comprises a non-random array of elements disposed on the surface of the gel.

It is further preferred that the gel absorbent layer have a void volume of 10–90%, Is preferably a void volume of 15–80%. Knowing the calipered thickness of a particular gel absorbent layer, the percentage of the apparent volume, which constitutes voids, can readily be calculated. The caliper of the gel may be measured with a conventional thickness gauge in which a pair of opposed feet respectively contacts the patterned face and smooth face (or second patterned face) of the layer. The foot contacting the patterned surface(s) being sufficiently broad to span several of the highest points on the patterned surface and thus lie in a plane tangential to the highest points of the patterned surface. The apparent volume of a unit area of gel layer is calculated as the product of area and calipered thickness. The calipered thickness of the gel layer is, of course, greater than the thickness of a gel layer having the same volume of polymer but with two smooth parallel faces.

The hydrophilic gel layer is generally between 250 and 5000 micrometers (~10 to 200 mils) in total thickness. It will be understood that hydrophilic gel layers in excess of 5000 micrometers may have a void volume that is less than 10%. Conversely, a gel layer thinner that 250 micrometers may have a void volume greater than 90%. In both of these cases, the patterned gel layer is still considered within the scope of the present invention.

As previously pointed out, the void volume constitutes about 10–90% the apparent volume of the gel absorbent layer, whether one or two surfaces are patterned. If the void volume falls below 10% of the apparent volume, the gel layer tends to possess the characteristics of conventional, unpatterned gel layer. On the other hand, if the void volume exceeds 90% of the apparent volume, the gel layer may lack sufficient structural integrity and may not be sufficiently absorbent.

The size of the individual pattern elements may be any suitable size that enhances the surface area of the gel, and which may swell to reduce the void volume of the gel layer. Generally the individual pattern elements are from about 100 to 15,000 micrometers, preferably about 1000–5000 micrometers in cross section (independently height and width dimensions) and have a repeat distance (i.e. that distance from one element to the next, peak to peak) of 100 to 15,000 micrometers, preferably about 1000–5000 micrometers as well. The minimal distance between adjacent elements may vary from 0 to 10,000 micrometers. Thus, there may be a flat, unpatterned surface area of absorbent between adjacent elements, or the elements may be continuous.

The wound exudate may be a viscous fluid that may not flow readily into narrow channels between protuberances, so the volume between pattern elements may be susceptible to clogging if not appropriately spaced. Similarly, if the pattern elements are depressions in the surface of the gel, the width of the depression should be sufficient to avoid clogging. For this reason the minimal distance of one protuberant pattern element to the next, or the width of the depression pattern element is preferably at least 250 micrometers and most preferably at least 750 micrometers.

If desired, a pattern may also be imparted to the outer face of the hydrophilic gel absorbent layer (i.e. the major surface of the absorbent layer that faces away from the wound surface). Imparting such a pattern increases the surface area of the gel layer and may promote greater evaporation of the fluid from the hydrophilic gel. The pattern may be the same or different than the pattern on the facing surface of the gel, as can the size of the pattern elements. Further, the individual elements on either surface of the gel layer may be protuberances extending form the surface, or may be depressions in the surface.

The pattern, whether protuberances or depressions, defines voids in the face of the gel layer. As will be understood, if the pattern elements are protuberances, the volume between the pattern elements defines the void volume. If depressions, the void volume is the volume of the pattern elements themselves. As the gel swells on contact with fluids such as exudate, the void volume may be reduced, depending on physical properties of hydrophillic gel. Advantageously, the void volume creates a low resistance path for the swelling of the hydrophilic gel layer, and consequently mushrooming and pressure on the wound is reduced.

If desired, the hydrophilic gel may be in direct contact with the wound and/or skin surface. However, if in direct contact, the pattern elements are preferably chosen to provide minimal direct contact with the wound or skin surface and further chosen so as to be non-adherent. Useful materials for direct contact include hydrocolloid and hydrogel absorbent materials.

The wound dressing of the present invention preferably comprises a porous or non-porous facing layer to provide a fluid permeable barrier between the wound site and the absorbent hydrophilic gel absorbent layer. The facing layer allows transport of moisture (i.e. fluid and vapor) from the wound to the patterned surface of the absorbent gel layer and may isolate the wound from other components of the dressing. The facing layer is preferably soft, flexible, conformable, non-irritating and non-sensitizing. Any of a variety of polymers may be used including polyurethane, polyethylene, polypropylene, polyamide or polyester materials. Further, the facing layer may be in the form of moisture vapor permeable films, perforated films, woven-, non-woven or knit webs or scrims. A preferred facing layer comprises a polyurethane film.

In one useful embodiment, the facing layer is conformable to animal (including human) anatomical surfaces, has a moisture vapor transmission rate of at least 300 grams per square meter per 24 hours at 80% relative humidity differential at 40° C. (per method of Chen, U.S. Pat. No. 5,733,570), is impermeable to liquid water throughout substantially its entire imperforate area and contains perforations means for passing wound exudate through the facing layer. This means that the facing layer does not pass liquid water under normal wound treatment conditions except at the places in the facing layer which are positively perforated to allow the exudate to pass into the reservoir.

The preferred moisture vapor transmission rate of the facing layer is at least 600 grams per square meter per 24 hours at an 80% relative humidity differential at 40° C. The facing layer may further comprise a pressure sensitive adhesive layer. The adhesive coated facing layer must have the aforesaid MVTR. Therefore, if the facing layer is impermeable to liquid water except for the perforation means, the adhesive can be permeable to liquid. water and vice versa. Porous or non-porous facing layers such as perforated polyurethane, polyamide, polyester, polypropylene, polyethylene, polyether-amide, polyurethanes, chlorinated polyethylene, styrene/butadiene block copolymers ("Kraton" brand thermoplastic rubber, Shell Chemical Company, Houston, Tex.) and polyvinyl chloride and those described in U.S. Pat. No. 3,121,021 that are covered with a pressure sensitive adhesive that is not permeable to liquid water can be used for the facing layer. Optionally these films can be perforated. Additional porous materials include woven and non-woven substrates.

It is preferred that the facing layer have the above mentioned moisture vapor or liquid permeability (1) so that maceration of the skin under the wound dressing does not occur, (2) so that moisture build-up under the facing layer does not cause the facing layer and, therefore, wound dressing to be lifted off the skin, and (3) to enhance proximation of the wound edges. Preferred facing layers are thin polymeric films optionally coated with pressure sensitive adhesive which, in combination, have the above characteristics.

The perforation means in the facing layer are holes or slits or other perforations that conduct the passage of liquid water or wound exudate from the wound into the absorbent layer of the wound dressing. The perforations may additionally extend through an adhesive layer, if the front surface of the facing film (that surface facing toward the wound) is coated with a pressure sensitive adhesive layer.

A backing layer may be present in all of the embodiments of the present invention. Preferably the backing layer is conformable to animal anatomical surfaces, impermeable to liquid water and has a moisture vapor transmission rate of at least 600 grams per square meter per 24 hours at an 80% relative humidity differential at 40° C. (per Chen, U.S. Pat. No. 5,733,570). The backing layer, in combination with a facing layer, may be constructed to form a reservoir (e.g. a pouch or envelope) that surrounds the hydrophilic gel absorbent layer, into which the exudate from the wound passes. This reservoir does not permit liquid water or exudate to pass out of it. Instead, the patterned gel layer absorbs the exudate, and moisture in the exudate passes through the backing layer in a vapor form into the atmosphere. The reservoir dressing permits wound exudate to be rapidly removed from the wound site and prevents liquids or bacteria from outside the dressing to contaminate the wound site.

In order to remove moisture vapor, the moisture vapor transmission rate of the backing layer is at least as above noted, and preferably at least 1200 grams per square meter per 24 hours at an 80% relative humidity differential at 40° C.

The preferred embodiments for the facing and backing layers are thin conformable polymeric films. Generally the films are from 12 to 50 microns in thickness, preferably from 12 to 25 microns. Conformability is somewhat dependent on thickness, thus the thinner the film the more conformable the film. Reference has been made herein to the films utilized in the wound dressing of the present invention being conformable to animal anatomical surfaces. This means that when the films of the present invention are applied to an animal anatomical surface, they conform to the surface even when the surface is moved. The preferred films are conformable to animal anatomical joints. When the joint is flexed and then returned to its unflexed position, the film stretches to accommodate the flexation of the joint but is resilient enough to continue to conform to the joint when the joint is returned to its unflexed condition.

Examples of films which are useful in applicant's invention as facing or backing layers include polyurethanes, such as ESTANE polyurethanes (available from B.F. Goodrich, Cleveland, Ohio), elastomeric polyester such as HYTREL™ polyester elastomer (E. I. duPont deNemours & Co., Wilmington, Del.), blends of polyurethane and polyester, polyvinyl chloride, and polyether-amide block copolymer, such as PEBAX available from Elf-Atochem. Particularly preferred films for use in the present invention are polyurethane and elastomeric polyester films. The polyurethane and elastomeric polyester films exhibit a resilient property that allows the films to have good conformability.

Particularly useful films include so called "spyrosorbent" films having a differential moisture vapor transmission rate (MVTR). Dressing incorporating spyrosorbent films not only manage wound exudate by absorption, but have the ability to adjust the moisture vapor transmission properties in response to the amount of exudate. Such spyrosorbent films are hydrophilic, moisture vapor permeable and have a relatively high MVTR (wet), and have a differential MVTR ratio (wet to dry) that is greater than 1, and preferably greater than 3:1. The dry MVTR is greater than about 2,600 g/m2/24 hrs, preferably about 3000 to 4000 g/m2/24 hrs. A particularly preferred spyrosorbent film, useful as a backing layer, is a segmented polyurethane such as a segmented polyether polyurethane urea based on polytetramethylene glycol and polyethylene glycol polyols. Such a spyrosorbent films are described in U.S. Pat. Nos. 5,653,699 and 4,849,458 (Reed et al.), incorporated herein by reference.

Many different constructions of an absorbent dressing are possible with the facing layer, the patterned, hydrophilic gel absorbent layer and the backing layer. In one embodiment, the areas of the facing layer and the backing layer are greater than that of the absorbent layer and the facing layer is bonded to the backing layer, thereby forming a pouch, with the absorbent disposed between the two. In another embodiment the one of the facing or backing layers may be substantially the same area as the absorbent layer, and the other of greater area. The greater area of the facing or backing layer forms a periphery to which an adhesive layer and a release liner may be attached. It will further be understood that the facing and/or backing layer may be attached or bonded to the adjacent surface of the absorbent layer to form a contiguous layer construction, in which the backing and facing layers may be the same or of greater area that the absorbent layer. Alternatively, the backing and facing layers may be bonded to each other, and may or may not be bonded to the absorbent layer. In these last constructions, the absorbent layer is constrained within a pouch created by the attachment of the facing and backing layers to each other. The layers may be bonded to each other by any conventional means such as adhesives, heat sealing, or other bonding means.

It is preferred that the facing, absorbent and backing layers of the present invention be at least translucent and more preferably sufficiently transparent so that the wound site to which they are applied can be viewed through the dressing. It is advantageous to view and evaluate the wound and healing thereof without removal of the wound dressing to avoid unnecessary handling of the wound site and exposure of the wound to the environment, which reduces the likelihood of contamination, and avoids the need to cleanse the wound as would be the case were the dressing to be removed. It is preferred that the dressing be both transparent and colorless so that the color of the wound, exudate, and periwound skin may also be evaluated. Preferred transparent films for use as facing and backing layers that allow visual inspection of the wound site include polyurethane films, such as ESTANE™ polyurethanes (B.F. Goodrich, Cleveland, Ohio); elastomeric polyesters, such as HYTREL™ polyester elastomers (E. I. duPont deNemours & Co., Wilmington, Del.; and, polyether block amides (PEBAX, Elf Altochem North America, Philadelphia, Pa.). Other useful films are those describes in U.S. Pat. Nos. 4,499,896; 4,598,004; and 5,849,325 (Heinecke et al), the disclosures of which are incorporated herein by reference.

While the facing layer can be attached to the wound by means other than a pressure sensitive adhesive on its surface, it is preferred to use such an adhesive. The presence of the adhesive of the facing layer normally reduces the moisture vapor permeability of the facing layer. Therefore it is preferred that the facing layer is adhesive coated prior to adding a plurality of perforations to the layer. The wound exudate therefore can readily pass through a perforated adhesive coated facing layer. Preferably, both the facing and backing layers are precoated with an adhesive layer to both facilitate bonding of the backing layer to the facing layer (forming a pouch), and bonding of the facing film to the wound site.

The facing layer is normally attached to the wound site by means of adhesive which can be continuous or pattern coated. The preferred adhesive which can be used with the wound dressings of present invention are the normal adhesives which are applied to the skin such as those described in U.S. Pat. No. Re. 24,906 (Ulrich), particularly a copolymer of 96% iso-octyl acrylate units and 4% acrylamide units and a copolymer of 94% iso-octyl acrylate units and 6% acrylic acid units. Other useful adhesives are those described in U.S. Pat. No. 3,389,827 that comprise block copolymers having three or more polymer block structures having a general configuration—A—B—A—wherein each A is a thermoplastic polymer block with a glass transition temperature above room temperature (i.e., above about 20° C.) having an average molecular weight between about 5000 and 125,000 and B is a polymer block of a conjugated diene having an average molecular weight between about 15,000 and 250,000. Additional examples of useful adhesives are acrylic adhesives such as iso-octyl acrylate/n-vinyl pyrrolidone copolymer adhesives and crosslinked acrylate adhesives such as for example those described in U.S. Pat. No. 4,112,213. Inclusion in the adhesive of medicaments is useful for enhancing wound healing and the inclusion of antimicrobial agents such as iodine is useful for preventing infection.

The adhesive may optionally be a microsphere adhesive with low trauma properties as described in U.S. Pat. No. 5,614,310; a fibrous adhesive with low trauma properties as described in U.S. patent application Ser. No. 08/980,541, filed Dec. 1, 1997; or have especially good adhesion to wet skin, such as the adhesives described in U.S. patent application Ser. No. 09/329,514, filed Jun. 10, 1999; and PCT Publication Nos. WO 99/13866 and WO 99/13865.

The adhesive may be chosen to be permeable to water or wound exudate, or the adhesive may be pattern coated on the front surface of the wound dressing (i.e. the surface in contact with the wound site, whether it is the front surface of the facing or backing layers) so as to not impede the flow of exudate to the absorbent layer, i.e. the adhesive may be coated at the periphery of the wound dressing. Alternatively the adhesive layer may be perforated as described for the facing film to provide a fluid path for the exudate.

A release liner may be attached to the adhesive layer for ease of handling. Examples of release liners are liners made of or coated with polyethylene, polypropylene and fluorocarbons and silicone coated release papers or polyester films. Examples of the silicone coated release papers are Polyslik S-8004, 83 pound (135.4 g/m$^2$) bleached silicone release paper supplied by H. P. Smith Co., Chicago, Ill., and 80 pound (130.5 g/m$^2$) bleached two-sided silicone coated paper (2-80-BKG-157) supplied by Daubert Chemical Co., Dixon, Ill.

The wound dressing may also comprise a frame that allows the dressing to be more easily applied to the wound. The frames are made of a relatively rigid material that maintains the shape of the dressing during handling and application to the wound site. The frame is generally releasably adhered to the back surface of the backing film and is removed after application of the wound dressing. Suitable frames are described in U.S. Pat. Nos. 5,531,855 and 5,738, 642 (Heinecke et al.) the disclosures of which are incorporated herein by reference.

The patterned surface may be imparted to the hydrophilic gel by conventional molding techniques. By this method, a hardenable, hydrophilic gel precursor composition, having desired viscosity, is deposited in a master negative mold, the gel precursor composition is allowed to harden (or otherwise set or cure) and the product patterned gel is removed from the mold. By hardenable gel precursor composition it is meant a composition that will cure, polymerize, crosslink, solidify, harden or set to produce a hydrophilic gel. The precursor composition may be a gel composition that is heated to a temperature sufficient that the gel has the desired viscosity, then subsequently cooled and hardened, or may be a composition which, when thermally or radiation cured, produces the desired hydrophilic gel.

The hydrophilic gel precursor may comprise a mixture of monomers such as the previously described hydrogel monomers, a solution of hydrogel polymer in hydrogel monomers or solvent, a solution of hydrocolloid optionally containing a hydrophobic polymer or precursor monomers to the hydrophobic polymer, or a solution of a hydrophilic polymer.

If desired the patterned gel may be prepared having an integral backing layer by depositing the gel precursor onto the master negative molding surface in an amount sufficient to fill the cavities of the master, moving a bead of the gel precursor between the master and the flexible backing film, then curing the gel.

The gel or precursor gel composition, deposited in the mold, should have a viscosity generally less than about 5,000 cps. Above that range, air bubbles may be entrapped and the gel (or precursor) may not completely fill the pattern of the master mold. However, inexact replication of the master mold pattern is normally acceptable, and minor blemishes, entrapped air bubbles or fractures in the hydrophilic gel layer will still be useful.

In some instances, the desired pattern may be imparted using an embossing technique. Hydrophilic gels suitable for embossing are those which behave as thermoplastic polymers, i.e. those that soften when exposed to heat and return to the original condition when cooled. By this method, the hydrophilic gel may be embossed by passing it between two rollers, at least one of which has a pattern of protuberances and/or depressions corresponding to the desired pattern on the hydrophilic gel. One or both rollers may be heated to a suitable temperature, the unpatterned gel is passed between the two rollers to impart the desired pattern, then the gel is cooled and the imparted patterned is retained. Generally only one roller has a pattern (which is the negative to the desired pattern imparted to the gel), while the other roller is smooth. If it is desired that both major surfaces of the gel be patterned, then both rollers may have patterned surfaces.

In a preferred embodiment, a patterned hydrogel layer may be prepared as follows. A patterned master negative mold is provided bearing the negative of the desired pattern. The master for use with the above described method may be a metallic master, such as nickel, nickel-plated copper or brass, although the master can also be constructed from thermoplastic materials, such as a laminate of polyethylene and polypropylene. A preferred master for use in the above-outlined method of the invention is a sheet of thermoplastic resin that is stable to the curing conditions and has been embossed by a metallic master tool such as nickel-plated copper or brass. Such a thermoplastic master is relatively inexpensive and yet can be used to form many patterned absorbent layers before becoming unduly worn.

When the thermoplastic master is made from a radiation-transparent thermoplastic material, the hydrophilic gel precursor can be cured by being irradiated through the master. By using a radiation-transparent master, integral backing layers for the cured hydrophilic patterned gels of the present invention can be opaque. When the master is made from a radiation-transparent thermoplastic resin such as a polyolefin, it is possible to prepare the patterned gels bearing patterns on both surfaces of the gel layer.

By being made of thermoplastic resin, the master can have a low-energy surface that affords good release from a cured gel. Good release is assured when there is a significant difference in surface energy between the surfaces of the master and the cured gel, the latter typically being about 40–41 dynes/cm. Because the surface energy of each of polypropylene and polyethylene is about 30–31 dynes/cm, these afford easy separation of the cured gel. Poly (vinylchloride) and cellulose acetate butyrate, both of which are about 39–42 dynes/cm in surface energy also provide good bonding with the cured gel but generally require a release agent. Polyolefins are more transparent to and stable towards ultraviolet radiation than are poly(vinylchloride) and cellulose acetate butyrate.

A particularly preferred material for use in a master is a laminate of polyethylene and polypropylene which has been embossed with the polyethylene layer in contact with the metallic master tool at a temperature above the softening point of the polyethylene and below that of the polypropylene. The polypropylene layer of the laminate affords the strength and flexibility needed to permit it to move a bead of the gel precursor across a rigid master negative molding surface, and the polyethylene layer provides a low glass transition temperature and melt temperature to facilitate replication of the original master tool. If the gel precursor is thermoplastic, the same master molds may be used. The gel precursor and/or the master negative mold may be heated to reduce the viscosity of the material to allow it to flow into the molding surface.

The hydrophilic gel precursor is added to the mold to cover the pattern and to fill the voids therein. If the hydrophilic gel precursor is to be thermally or radiation cured, it is desirable to cover the exposed surface with a radiation transparent film or release liner to exclude atmospheric oxygen from the gel precursor, which would tend to interfere with the curing. The gel precursor is added to the mold in amount sufficient to cover the pattern, and achieve the desired thickness and void volume in the product patterned gel.

Curing conditions, whether the gel precursor is radiation or thermally cured, are well known in the art. Any conventional curing conditions, as well as any conventional free-radical initiators may be used.

After curing (or after the precursor gel has cooled and hardened if thermoplastic), the patterned hydrophilic gel is removed from the mold and preferably the patterned surface is placed in contact with a release liner. The construction, having the patterned gel sandwiched between two release liners may then be easily handled and converted to the desired size and shape for subsequent use in a wound dressing.

Once converted, the release liners may be removed and the exposed surfaces of the patterned gel (both the patterned front surface and the opposite, generally unpatterned, back surface) may be laminated to the facing and backing films respectively. The backing and facing films, previously described, may be of any suitable size and shape for use in a wound dressing. The hydrophilic gel layers are normally slightly tacky, so the facing and backing films readily adhere to the major surfaces of the hydrophilic gel layer. Optionally, the facing and backing film layers may be precoated with adhesive layers, and optionally a release liner as previously described.

Alternatively, the gel precursor may be covered with the backing film, cured (or allowed to cool and solidify) and the composite patterned gel article, having an integral backing film, is removed from the master mold. This patterned gel article may then be laminated to the facing film, and converted to the desired size and shape. As yet another alternative, no release liners may be used, and the gel may be removed from the mold and placed between the backing and facing films.

In any of the foregoing methods, the facing and backing films are generally adhered to each other at the periphery of the hydrophilic gel layer to produce a composite article comprising a backing layer, a facing layer, and a patterned hydrophilic gel layer disposed between the two. In such a construction the facing and backing layers, sealed at their periphery, form a reservoir with the patterned absorbent gel layer disposed between the two.

FIG. 1 shows a cross-section of a wound dressing of the invention. Wound dressing 10 comprises a patterned hydrophilic absorbent gel layer 12 having a front patterned surface 14. The patterned depicted is a regular, repeating series of protuberances and depressions, the protuberances being substantially triangular in cross-section and the depressions being substantially truncated pyramids in cross section. Other patterns may be used as previously described. The back surface 16 of gel layer 12 may be unpatterned as shown, but a pattern may be imparted to surface 16 to promote greater evaporation. The gel layer 12 is disposed between backing layer 18 and facing layer 20. As shown, both backing layer 18 and facing layer 20 have a greater area than gel layer 12 to form a periphery 22 at which backing and facing layers may be bonded to each other. The facing layer 20 is permeable to wound exudate and preferably has a plurality of apertures 24 therethrough to conduct exudate from the wound surface to the absorbent layer 12. Dressing 10 may further include an adhesive layer 26 for securing dressing to the wound site. As depicted, the adhesive layer covers substantially the entire wound-facing surface of facing layer 20. In such constructions, It will be understood that the apertures would further extend though both the facing layer and the adhesive layer. It will be understood that adhesive layer 26 may be coated on only a portion of the wound dressing. For example, the adhesive layer may be coated on the periphery 22. The wound dressing 10 may further comprise a frame 28 to provide temporary support to the wound dressing during application. Frame 28, if present, is generally removably adhered to the wound dressing to facilitate removal after application of the wound dressing to the wound site.

EXAMPLES

The following examples are offered to aid in understanding of the present invention and are not to be construed as limiting the scope thereof. Unless otherwise indicated, all parts and percentages are by weight.

TEST PROTOCOLS
Liquid Absorbency and Moisture Vapor Transmission

A Test Cell for measuring Liquid Absorbency (LA, the amount of liquid absorbed by a wound dressing sample) and Moisture Vapor Transmission (MVT, the amount of moisture vapor transmitted from a wound dressing sample) was constructed as follows. A cylindrical-shaped block (7.6-cm diameter, 2.5-cm height) of transparent polycarbonate was cut to form a cylindrical-shaped cavity (3.8-cm diameter, 1.3-cm depth, 14-ml volume capacity) in the bottom center of the block and a threaded exit hole (1-cm diameter, 1.2-cm length extending to the cavity) in the top center of the block. A removable bolt was used to open or close the inlet as necessary. The following test procedure was used to measure LA and MVT of a wound dressing sample. The weight ($S_0$) of the dry pouch-dressing sample (without release liner) was measured. The dry sample (adhesive side up) was then centered under the Test Cell and adhered to the bottom surface of the Cell. The sample was positioned such that the cavity of the Cell was directly above the center of the dressing. A known weight ($L_0$, about 14 g) of Calf Serum Bovine liquid (CSB liquid, Sigma-Aldrich Chemical Co., Milwaukee, Wis.) was added by syringe through the inlet and into the Cell cavity. The bolt was screwed into the inlet and the entire Cell plus Sample (including bolt) was weighed ($CS_0$) and placed on an aluminum tray in an oven maintained at 40° C. and 20% RH. At various time intervals, the Cell+Sample was removed from the oven and weighed ($CS_x$, where x is the test duration in hours). Additionally, the CSB liquid was removed from the Cell cavity with a syringe, weighed ($L_x$, where x is the test duration in hours), and returned to the Cell cavity. The entire Cell plus Sample was then returned to the oven until the duration of the test period.

$MVT_x$ (in grams of liquid transpired from sample at x hours), $LA_x$ (in grams of liquid absorbed by sample at x hours), and % $LA_x$ (percent increase in weight of sample at x hours) were then calculated as follows:

$MVT_x = CS_0 - CS_x$ $LA_x = L_0 - L_x - MVT_x$

% $LA_x = 100 \, (LA_x) \div S_0$

Comparative Example A
Pouch-Type Absorbent Dressing

A pouch-type absorbent dressing was constructed according to the following procedure.

A 1-mm thick transparent, absorbent layer comprised of copolymerized MPEG 400 acrylate (70%; Shin Nakamora, Wakayama City, Japan) and acrylic acid (30%; BASF, Mount Olive, N.J.) was prepared according to the "General Polymerization Process" as described in U.S. Pat. No. 5,733,570 (Chen et al.). A 3.8-cm diameter circular pad was cut from the absorbent sheet and hand laminated to the center of a 7.6-cm diameter circular sample of 0.025-mm thick polyurethane facing film layer[extruded from ESTANE™ 58237 resin (B. F. Goodrich, Cleveland, Ohio) as described in U.S. Pat. No. 4,499,896 (Heinecke) that was supported on standard silicone-treated release liner. A 7.0-cm square sample of the same polyurethane film was then centered over the top of the absorbent layer, to create a backing film layer and heat-sealed along the entire periphery to the upper surface of the facing film layer. A skin contact adhesive comprising isooctyl acrylate (97%)/acrylamide (3%) copolymer may be prepared as described in Example 9 of U.S. Pat. No. Re. 24,906 (Ulrich) was then hand laminated to the outer 3.8-cm edge of the lower surface of the facing film layer, thereby forming a pouch with the absorbent layer disposed between the facing and backing film layers. The completed pouch dressing (4.62 g) was evaluated for liquid absorption and water vapor transmission. The results are shown in Table 1. The dressing was observed to remain clear when hydrated. The free swell absorbency was about 1100%.

Comparative Example B
Pouch-Type Absorbent Dressing with Perforations

A pouch-type absorbent dressing with perforations was constructed according to the following procedure.

A 7.6-cm diameter circular sample of TEGADERM™ 1626W standard transparent dressing with release liner (3M Company, St. Paul, Minn.) was perforated such that a square pattern of nine 1.6-mm diameter perforations, spaced equally apart by about 6 mm, was centered on the sample, forming a perforated facing film layer. A 3.8-cm diameter circular absorbent layer (as described in Comparative Example A) was hand laminated to the center of the non-adhesive side of the TEGADERM™ sample so that the pad entirely covered the perforated region of the facing film layer. A 7.0-cm square sample of polyurethane film (ESTANE™ 58237) was then centered over the top of the absorbent pad and heat-sealed to the facing TEGADERM™ film layer as described in Comparative Example A. The completed pouch dressing (3.7 g) was evaluated for liquid absorption and water vapor transmission. The results are shown in Table 1. The dressing was observed to remain clear when hydrated.

Comparative Example C
Pouch-Type Absorbent Dressing with Perforations

A pouch-type absorbent dressing with perforations was constructed according to the following procedure.

A 10-cm×12-cm sample of TEGADERM™ 1626W standard transparent dressing with release liner was perforated such that a square pattern of twenty-five 1.5-mm diameter perforations, spaced equally apart by about 10 mm, was centered on the sample. A 7.6-cm diameter circular absorbent layer (as described in Comparative Example A) was hand laminated to the center of the nonadhesive side of the TEGADERM™ sample so that the layer entirely covered the perforated region of the facing film layer. A 10-cm×12-cm sample of TEGADERM™ 9536 HP transparent dressing (3M Company) with release liner removed was then centered over the top of the absorbent layer and adhesively sealed by finger pressure to both the absorbent pad and to the upper surface of the facing film layer. The completed pouch dressing (4.2 g) was evaluated for liquid absorption and water vapor transmission. The results are shown in Table 1. The dressing was observed to remain clear when hydrated.

Example 1
Pouch-Type Dressing with Patterned Absorbent Layer

A pouch-type absorbent dressing with perforations and a patterned absorbent layer was constructed according to the procedure described in Comparative Example B, except that a different absorbent layer had a patterned surface facing the perforations of the facing film layer. The patterned absorbent layer was prepared according to the following procedure.

Monomer Solution A was prepared by mixing lauryl acrylate (6.0 g, Henkel, Cincinnati, Ohio), MPEG 400 acrylate (68 g, Shin Nakamora) and IRGACURE™ 184 (0.12 g, Ciba Geigy Co., Terrytown, N.Y.), and stirring the resulting solution for 30 minutes. Monomer Solution B was prepared by mixing acrylic acid (80 g, BASF), a 50% sodium hydroxide solution (15 g), and distilled water (5 g), and stirring the resulting solution for 30 minutes. Monomer Solution B (26 g) was added to Monomer Solution A with stirring for 30 minutes. The resulting homogeneous mixture was poured onto the surface of a silicone rubber mold to a depth of 1.25 mm, covered with a siliconized polyester film (Liner Grade 10256, Rexam Release. West Chicago, Ill.) and cured for 15 minutes under four GTE Sylvania 350 Blacklight bulbs at a distance of 7.5 cm. The silicone rubber mold was constructed with a serrated patterned surface having triangle-shaped channels about 0.5-mm in depth and about 1.3 mm apart (peak-to-peak). After curing, the polyester film was removed and the polymerized material was stripped from the silicone mold. A 3.8-cm diameter pad was cut from the material for use in the construction of the dressing. The completed pouch dressing (3.3 g) was evaluated for liquid absorption and water vapor transmission. The results are shown in Table 1. The dressing was observed to remain clear when hydrated. The void volume was 25%, and the free swell absorbency was 844% swell.

Example 2
Pouch-Type Dressing with Patterned Absorbent Layer

A pouch-type absorbent dressing with perforations and a surface-patterned absorbent layer was constructed according to the procedure described in Example 1, except that the lower surface of the absorbent layer (facing the perforations of the facing film) was patterned with a rectangular array of cylinder-shaped projections. The silicone rubber mold was constructed with a patterned surface having cylinder-shaped depressions about 1.0-mm in diameter and 1.0-mm in height. The spacing between the cylinders was about 2.5-mm center-to-center. The completed pouch dressing (2.6 g) was evaluated for liquid absorption and water vapor transmission. The results are shown in Table 1. The dressing was observed to remain clear when hydrated. The void volume was 42%.

Example 3
Pouch-Type Dressing with Patterned Absorbent Layer

A pouch-type absorbent dressing with perforations and a patterned absorbent layer was constructed according to the procedure described in Comparative Example C, except that a different absorbent layer was used that had a patterned surface (facing the perforations of the facing film layer) patterned with a channeled surface. The patterned absorbent layer was prepared according to the procedure described in Example 1. The completed pouch dressing (2.7 g) was evaluated for liquid absorption and water vapor transmission. The results are shown in Table 1. The dressing was observed to remain clear when hydrated. The void volume was 25%.

Example 4
Pouch-Type Dressing with Patterned Absorbent Layer

A pouch-type absorbent dressing with perforations and a patterned absorbent layer was constructed according to the procedure described in Example 3, except that the silicone rubber mold used to prepare the absorbent layer was constructed with a serrated patterned surface having trapezoidal-shaped channels about 0.5-mm in depth and about 4.5 mm apart (peak-to-peak) (See FIG. 1). The completed pouch dressing (6.6 g) was evaluated for bovine liquid and water vapor transmission. The results are shown in Table 1. The dressing was observed to remain clear when hydrated. The void volume was 37%.

Comparative Example D
Pouch-Type Absorbent Dressing with Perforations

A pouch-type absorbent dressing with perforations was constructed according to the procedure described in Example 4, except that the surface of the absorbent layer was flat, i.e., not patterned. The completed pouch dressing (9.0 g) was evaluated for liquid absorption and water vapor transmission. The results are shown in Table 1. The dressing was observed to remain clear when hydrated.

TEST DATA

Samples from Comparative Examples A–D and Examples 1–4 were evaluated for liquid absorbency and moisture vapor transmission. The results are shown in Table 1 along with results for the commercial DUODERM™ CGF wound dressing (ConvaTech, Montreal, Canada; dry weight=6.8 g). It is noted that the variation in weights of the exemplified dressings (Examples 1–4 and Comparative Examples A–D) is a function of varying thickness resulting from being hand-made in the laboratory using different molds.

TABLE 1

| Example | Test Duration (Hours) | Liquid Absorbency Grams | Liquid Absorbency Percent | Moisture Vapor Transmission (Grams) |
|---|---|---|---|---|
| Comparative A | 24 | 4.3 | 93 | 0.43 |
| Comparative B | 22 | 8.6 | 232 | 5.0 |
| Comparative C | 24 | 8.5 | 202 | 1.0 |
| Comparative D | 4 | 1.0 | 11 | 0.1 |
| Comparative D | 5.75 | 1.5 | 17 | 0.15 |
| 1 | 6 | 6.5 | 197 | 0.5 |
| 2 | 8 | 8.0 | 308 | 0.7 |
| 3 | 19 | 8.74 | 324 | 2.15 |
| 4 | 4 | 9.0 | 136 | 1.0 |
| 4 | 5.75 | 15.6 | 236 | 1.42 |
| DUODERM ™ CGF | 24 | 2.2 | 32 | 0.12 |

During test evaluations, the absorbent layers of Comparative Examples B, C, and D were observed to "mushroom" through the perforations and many pieces of the swollen pad passed through the perforations. In contrast to the Comparative Examples B–D (smooth-surfaced absorbent layer and perforations in facing film layer), the absorbent layer of Examples 1–4 (having a patterned surface) were observed to absorb fluid more rapidly due to their wicking ability. It appeared that a greater area of the patterned surfaces was utilized more efficiently in absorbing the fluid. The patterned surfaces also showed little or no "mushrooming" of material through the facing film layer perforations and improved dressing clarity. The open spaces or gaps present at the interface of the patterned surfaces and the facing film layers appeared to relieve internal pressure caused by the fluid absorption and this resulted in a less rippled appearance of the dressing as a whole.

The data in Table 1 support the conclusion that pouch dressings having an absorbent layer with a patterned lower surface have significantly greater liquid absorption and moisture vapor transmission than do similar dressings without a patterned (i.e., smooth and flat) lower surface. For example, compare the test results of Example 4 with Comparative Example D, two dressings that are identical except that Example 4 has a patterned absorbent layer and Comparative Example D does not. Overall, as shown in Table 1, Example 4 had about 9–10 times greater liquid absorbency and about 9–10 times greater moisture vapor transmission than Comparative Example D.

Example 5
Square Post Patterned Absorbent

A pouch-type absorbent dressing with perforations and a pattern surface was constructed as in Example 4 with the exception that the square projections protruded from the surface of the absorbent. The projections were in a symmetrically square array with each projection 10 mm. from its closest neighbor. Each projection was 2.5 mm. on each side and 1 mm. in height. This geometrical arrangement produces a 47% void volume percentage. When placed in fluid. the dressing exhibited good absorption and transparency.

Example 6
Square Post Patterned Absorbent

An absorbent construction of similar to that in Example 5 was prepared with the exception that the symmetrically square array had projections separated by 0.5 mm. This arrangement produced a 15% void volume percentage. Good fluid absorption and transparency was noted when the sample was brought into contact with saline fluid.

Example 7
Large Hexagon Patterned Absorbent

A symmetric array of hexagons, 10 mm. on each side, 1 mm. in height, and separated by 7.5 mm. from the neighboring hexagon, was prepared as an absorbent layer. This geometry produced a 15% void volume percentage. Construction of a dressing was similar to that in Example 4. This geometry as a patterned absorbent also exhibited good transparency and saline absorption behavior.

Example 8
Small Hexagon Patterned Absorbent

The symmetric array consisted of hexagons having sides of 2 mm., height of 1 mm. and a separation of 2 mm. from its closest neighbor. This results in a 18% void volume. A dressing prepared as in Example 4 using this hexagonal array showed transparency and saline absorption.

Example 9
Small Oval Patterned Absorbent

An absorbent was prepared consisting of a symmetrical array of ovals, 3.5 mm. in the major axis, 1.5 mm. in the minor axis, 1 mm. in height, and a 1 mm. minimum separation from its closest neighbor. This arrangement produced a 21% void volume. A dressing prepared as in Example 4 using this patterned structure exhibited good saline absorption and transparency.

Example 10
Large Oval Patterned Absorbent

A symmetrical oval array consisted of individual ovals each 7 mm. in the major axis, 2.5 mm. in the minor axis, 1 mm. in height, and separated by a minimum of 1 mm. from the nearest neighbor. The pattern was prepared so that the absorbent material in the interstices of the ovals was protruding so that the oval structures were indented into the surface of the absorbent. This produced a 26% void volume. This patterned absorbent, when prepared into a dressing as in Example 4, showed good saline absorption characteristics.

Example 11
Crosshatch Patterned Absorbent

A crosshatch pattern of absorbent material was prepared consisting of ribs arranged in 1.5 mm. square arrays and 0.5 mm. in width. This resulted in a 28% void volume. A dressing prepared as in Example 4 and using the geometrical structure exhibited good transparency and absorption behavior.

Example 12

An absorbent composition consisting of 2-ethylhexylacrylate/N,N-dimethylacrylamide/MPEG 400 acrylate in a 15/35/50 ratio with 0.14% IRGACURE 2959 was prepared. The patterned surface, curing conditions, and method of dressing preparation of Example 1 were followed to produce a structured absorbent composition and dressing. When placed in contact with saline fluid, the absorbent exhibited good fluid uptake and transparency was retained.

Example 13

A 20/20/60 ratio of 2-ethylhexylacrylate/hydroxyethyl acrylate/MPEG 400 acrylate with 0.14% IRGACURE 2959 was prepared. The procedure of Example 1 was followed to prepare the absorbent and dressing. The dressing exhibited good transparency in both the dry and fluid swollen conditions.

What is claimed is:

1. An absorbent dressing comprising a preselected, patterned, hydrophilic gel absorbent layer comprising pattern elements having a width and height of, independently, from 100 to 15,000 micrometers.

2. The absorbent dressing of claim 1 further comprising a permeable facing layer.

3. The absorbent dressing of claim 1 further comprising a backing layer.

4. The absorbent dressing of claim 1 further comprising a pressure sensitive adhesive layer to secure the dressing to a skin surface.

5. The absorbent dressing of claim 1 wherein said absorbent layer comprises a hydrocolloid dispersed in a hydrophobic polymer matrix.

6. The absorbent dressing of claim 5 wherein said absorbent layer comprises 20 to 50 percent by weight of a hydrophobic polymer and 80 to 50 percent by weight of a hydrocolloid.

7. The absorbent dressing of claim 5 wherein said hydrophobic polymer is an elastomeric polymer or copolymer.

8. The dressing of claim 1 wherein both major surfaces of the absorbent layer are patterned.

9. An absorbent dressing comprising:
- a permeable facing layer having a layer of pressure sensitive adhesive on at least a portion of the front surface of the facing layer,
- a backing layer bonded to said facing layer at the periphery,
- a hydrophilic gel absorbent layer having a preselected, patterned front surface disposed between the backing and facing layers, wherein pattern elements of said preselected, patterned front surface having a width and height of, independently, from 100 to 15,000 micrometers.

10. The absorbent dressing of claim 9 wherein the backing layer is permeable to moisture vapor.

11. The absorbent dressing of claim 9 wherein said patterned surface comprises protuberances extending from the surface of the hydrophilic gel absorbent layer.

12. The absorbent dressing of claim 9 wherein said patterned surface comprises depressions extending into the surface of the hydrophilic gel absorbent layer.

13. The absorbent dressing of claim 12 wherein said depressions comprise apertures extending through the thickness of the absorbent layer.

14. The absorbent dressing of claim 9 wherein said pattern defines a void volume on the surface of the absorbent layer, said void volume comprising 10 to 90% of the absorbent layer volume.

15. The absorbent dressing of claim 9 wherein said pattern is imparted by molding, casting or embossing.

16. The absorbent dressing of claim 9 wherein said pattern element of said patterned front surface is selected from truncated or untruncated ridges, channels, mounds, peaks, hemispheres, pyramids, cylinders, cones, blocks, and combinations thereof.

17. The dressing of claim 16 wherein said pattern elements are from about 1000–5000 micrometers in cross-section and have a repeat distance of 100 to 15,000 micrometers.

18. The absorbent dressing of claim 9 further comprising a release liner secured to said adhesive layer.

19. The absorbent dressing of claim 9 wherein the hydrophilic gel absorbent layer is selected from the group of hydrocolloids, hydrogels and hydrophilic polymers.

20. The dressing of claim 19 wherein said hydrogel is selected from polymers and copolymers of acrylic esters, methacrylic acid esters, substituted and unsubstituted acrylamides, methacrylamides, hydroxyalkyl (meth) acrylates, and N-vinylpyrrolidinone.

21. The absorbent dressing of claim 9 wherein the backing layer, facing layer and hydrophilic gel layers are transparent.

22. The absorbent dressing of claim 9 having a moisture vapor transmission rate of at least 300 $g/m^2/24hrs$.

23. The absorbent dressing of claim 9 wherein said adhesive is selected from acrylic adhesives.

* * * * *

UNITED STATES PATENT AND TRADEMARK OFFICE
CERTIFICATE OF CORRECTION

PATENT NO. : 6,566,575 B1
DATED : May 20, 2003
INVENTOR(S) : Stickels, Steven C.

It is certified that error appears in the above-identified patent and that said Letters Patent is hereby corrected as shown below:

Column 4,
Line 9, after "is" delete ".".

Column 7,
Line 25, after "10-90%," delete "Is".

Column 9,
Line 13, after "liquid" delete ".".

Column 18,
Line 67, delete "layer" and insert in place thereof -- layers --.

Column 19,
Line 34, after "fluid" delete ".".

Column 21,
Line 10, delete "having" and insert in place thereof -- have --.

Signed and Sealed this

Twelfth Day of April, 2005

JON W. DUDAS
*Director of the United States Patent and Trademark Office*